US005254459A

United States Patent [19]
Patarroyo
[11] Patent Number: 5,254,459
[45] Date of Patent: Oct. 19, 1993
[54] NUCLEOTIDE AND AMINO ACID SEQUENCES OF PROTEIN MTP40 OF *M. TUBERCULOSIS* AND SYNTHETIC PEPTIDES DERIVED THEREFROM

[76] Inventor: Manuel E. Patarroyo, Calle 135 No.15-40, Bogota, Colombia

[21] Appl. No.: 940,468

[22] Filed: Sep. 4, 1992

Related U.S. Application Data

[62] Division of Ser. No. 572,171, Aug. 23, 1990, Pat. No. 5,171,839.

[51] Int. Cl.$^5$ ...................... C12Q 1/68; G01N 33/569

[52] U.S. Cl. ........................................ 435/6; 435/732; 435/810; 435/863; 530/350; 530/326; 536/23.7; 536/24.32; 436/63; 436/808; 424/92

[58] Field of Search .................. 530/350; 435/6, 7.32, 435/863, 810; 424/92; 436/63, 808

[56] References Cited

U.S. PATENT DOCUMENTS 4,689,397 8/1987 Shinnick et al. .................... 530/327

OTHER PUBLICATIONS

Parra et al., Infection and Immunity, 59 3411-3417 (1991).

del Portillo et al., J. Clin. Microbiol., 29, 2163-2168 (1991).

Shinnick et al., "Isolation and Restriction Site Maps of . . . " Infection and Immunity, 55 (7); 1718-1721 (Italy 1987).

Engers et al., "Results of a World Health Organization—Sponsored . . ." Infection and Immunity, 51; 718-720 (Feb. 1986).

Verbon et al., J. of Bacteriology, 174, pp. 1352-1359 (1992).

Young et al., Molec. Microbiology, 6 (2); 133-145 (1992).

*Primary Examiner*—Robert A. Wax

*Assistant Examiner*—Rebecca Prouty

*Attorney, Agent, or Firm*—Abelman Frayne & Schwab

[57] ABSTRACT

The present invention relates to novel chemically synthesized nucleotides and novel chemically synthesized peptides which have been found to be effective in assaying for the presence of *M. tuberculosis.*

10 Claims, No Drawings

NUCLEOTIDE AND AMINO ACID SEQUENCES OF PROTEIN MTP40 OF *M. TUBERCULOSIS* AND SYNTHETIC PEPTIDES DERIVED THEREFROM

This is a division of application Ser. No. 572,171 filed on Aug. 23, 1990, now U.S. Pat. No. 5,171,839.

BACKGROUND OF THE INVENTION

This invention relates generally to the chemical synthesis of certain novel nucleotide sequences and novel synthetic peptides and, more particularly, to their use in diagnostic tests for *M. tuberculosis* and their immunoprophylactic value.

Tuberculosis is a serious infectious disease which affects 30 million people worldwide, especially in the developing countries (World Health Organization, Bull. WHO, 61, 779, 1983).

The diagnosis of tuberculosis relies on the observation of acid-fast bacilli in clinical specimens and on PPD (Purified Protein Derivative), a delayed type cutaneous hypersensitivity test (DCH). However, very often the number of bacterial cells in the sample is insufficient to make a successful diagnosis of the disease. On the other hand, the utility of PPD is limited both by its lack of specificity and by its inability to distinguish between an active disease state, previous sensitization by contact with *M. tuberculosis*, or cross-sensitization to other mycobacteria. The use of peptides as tools in the diagnosis of mycobacterial diseases was discussed recently in the First Vaccilep Workshop on the Immunology of Leprosy. (Immunology today. 10: 218-221, 1989.) The application of this strategy to tuberculosis would enable the production of highly specific and very stable reagents, at low cost, which could be used in immunoassays of excellent reproducibility. This type of easy-to-perform test would be useful in both seroepidemiological and clinical studies, looking to tuberculosis control and prevention. Besides, much attention has been focused on the use of nucleic acid probes to specifically detect a mycobacterial infection.

BCG (Bacillus Calmette Guerin) has been the most widely used vaccine around the world. However, it has not been possible to clearly demonstrate its protective value in all the immunization trials carried out to date.

The knowledge of individual antigens of *M. tuberculosis* is very important in the search for immunoprophylactic molecules and in the detection of specific molecules, i.e., antigens, exclusively present in *M. tuberculosis*. Such type molecules could be used in the design of reagents to accurately diagnose a tuberculosis infection, both at the DNA and the protein level, thus circumventing the cross-reactivity problems associated with the current diagnostic tests, and also they could serve as potential vaccines against this threatening disease.

The application of recombinant DNA techniques to the study of *M. tuberculosis* genes, has provided the complete nucleotide sequences which encode proteins of 71 kDa, 65KD, 38KD, 32KD and 19KD. Despite the fact that many of these genes encode for *M. tuberculosis* antigens which belong to the group of ubiquitous Heat Shock Proteins, immunological studies have demonstrated the presence of some epitopes of these molecules, most of which are capable of eliciting cellular responses "in vitro".

SUMMARY OF THE INVENTION

The present invention contemplates the description of a nucleotide sequence. Within this sequence there is a gene, 402 bp long, which encodes for a *M. tuberculosis* protein. The encoding nucleotide sequence is written from left-to-right, following the 5' to 3' direction of the encoding string of the gene in Formula I below. The meanings of the abbreviations employed in Formula I are: A: Adenine, C:Cytosine, G:Guanine, T:Thymine.

Formula I

ATGCTCGGCAACGCGCCGTCGGTGGTTCCCAACACCACGTTAGGGATGCACTGCGGCAGC

TTCGGCAGCGCTCCCAGCAACGGGTGGCTCAAGTTGGGTCTGGTCGAATTCGGTGGAGTC

GCAAAGTTGAACGCTGAGGTCATGTCGCCAACCACGCCGTCGCGCCAGGCGGTCATGTTG

GGAACCGGCACGCCGAACCGGGCGCGAATCAACTTCAATTGCGAGGTGTGGTCGAACGTG

TCGGAGACCATCAGCGGGCCGCGGCTGTACGGCGAAATGACAATGCAGGGAACGCGAAAA

CCCAGACCGAGCGGACCACGAATGCCACCGGACCCGGGTACTGCGTCGATGTTGGGCACC

GTGACGAATTCGCCGGGTGTCCCGGCGGTGCCGTGGGGGGCGTGA.

Oligonucleotide sequences derived from this sequence can be used as probes in hybridization or PCR assays, in order to accurately detect *M. tuberculosis* bacilli in clinical samples, such as, blood, serum and plasma, where their presence is suspected.

Synthetic oligonucleotides derived from this nucleotide sequence or from its complementary strand (A per T, T per A, G per C and C per G) may be used as primers to amplify the entire gene or any of its fragments and thus to detect even a few bacilli in a clinical sample. The use of the nucleotide sequences represented by Formula II and Formula III (see below), as well as any other sequence derived from Formula I or its complementary strings (A per T, T per A, G per C and C per G), for "in vitro" DNA amplification tests, as occurs in PCR, are also to be considered as an embodiment of the present invention.

5'CAACGCGCCGTCGGTGG3' denominated PT2 Formula II

5'CCCCCCACGGCACCGC3' denominated PT2 Formula III

The gene found in this region encodes for a specific *M. tuberculosis* protein, called MTP40, whose amino acid sequence is set forth in Formula IV. (The amino acids in Formula IV and also in Formulas V, VI, VII, VIII and IX which follow are named according to the letter codes which are defined hereinafter).

Formula IV

Met—Lys—Gly—Asn—Ala—Pro—Ser—Val—Val—Pro—Asn—Thr—Thr—Leu—Gly—

Met—His—Cys—Gly—Ser—Phe—Gly—Ser—Ala—Pro—Ser—Asn—Gly—Trp—Leu—

Lys—Leu—Gly—Leu—Val—Glu—Phe—Gly—Gly—Val—Ala—Lys—Leu—Asn—Ala—

Glu—Val—Met—Ser—Pro—Thr—Thr—Pro—Ser—Arg—Gln—Ala—Val—Met—Leu—

Gly—Thr—Gly—Thr—Pro—Asn—Arg—Ala—Arg—Ile—Asn—Phe—Asn—Cys—Glu—

Val—Trp—Ser—Asn—Val—Ser—Glu—Thr—Ile—Ser—Gly—Pro—Arg—Leu—Tyr—

Gly—Glu—Met—Thr—Met—Gln—Gly—Thr—Arg—Lys—Pro—Arg—Pro—Ser—Gly—

Pro—Arg—Met—Pro—Pro—Asp—Pro—Gly—Thr—Ala—Ser—Met—Leu—Gly—Thr—

Val—Thr—Asn—Ser—Pro—Gly—Val—Pro—Ala—Val—Pro—Trp—Gly—Ala

The present invention contemplates the entire protein encoded in Formula I, which means the amino acid sequence shown in Formula IV, or fragments thereof, produced as recombinant proteins in any type of expression vector, or as chemically synthesized peptides, which may be useful in immunoprophylactic or immunodiagnostic assays. Therefore, the synthetic peptides derived from the amino-acid sequence under Formula IV are also contemplated as an embodiment of this invention. The polypeptides contain about 16 to about 21 amino acid residues, including the amino acid residue sequence, written from left-to-right and in the direction of the amino-terminus to the carboxy-terminus, represented by the Formulas V, VI, VII, VIII and IX as set forth below.

| | |
|---|---|
| Met-Leu-Gly-Thr-Gly-Thr-Pro-Asn-Arg-Ala-Arg-Ile-Asn-Phe-Asn-Cys | (V) |
| Ile-Asn-Phe-Asn-Cys-Glu-Val-Trp-Ser-Asn-Val-Ser-Glu-Thr-Ile-Ser-Gly-Pro-Arg-Leu-Tyr | (VI) |
| Trp-Leu-Lys-Leu-Gly-Leu-Val-Glu-Phe-Gly-Gly-Val-Ala-Lys-Leu-Asn-Ala-Glu-Val-Met-Ser | (VII) |
| Ala-Ser-Met-Leu-Gly-Thr-Val-Thr-Asn-Ser-Pro-Gly-Val-Pro-Ala-Val-Pro-TrpGly-Ala | (VIII) |
| Gly-Pro-Arg-Leu-Tyr-Gly-Glu-Met-Thr-Met-Gln-Gly-Thr-Arg-Lys-Pro-Arg-Pro-Ser-Gly-Pro | (IX) |

The peptides represented by formulas V, VI, VII, VIII and IX were tested in serological and lymphocyte proliferation assays. From the results obtained, the peptides of Formulas V and VI showed promise as antigens in the development of an accurate diagnostic method, and the peptides of Formulas VI, VII, VIII and Ix each showed promise as a synthetic tuberculosis vaccine. It is to be understood that the use of any of these peptides, or any peptide derived from Formulas IV–IX, inclusive, in any type of diagnostic or immunoprophylactic tests, or in the design of a molecule with immunoprophylactic value as a vaccine against tuberculosis, is also comprehended as being embodied by the present invention.

These peptides are capable, when injected in an effective amount into a mammalian host, of inducing production of antibodies that immunoreact to an antigen of M. tuberculosis.

This invention also comprehends and includes the antigenically related variants of the polypeptides, for example, those polypeptides which include cysteine (Cys) or glycine (Gly) residues at their amino-terminus, or their carboxy-terminus, or both termini, or synthetic multimers containing a plurality of joined synthetic polypeptides wherein at least one of the repeating units is one of the polypeptides described above. The repeating units may be joined in a head-to-tail manner by amide bonds, or they may form polymeric multimers by the use of intra or intermolecular cysteine disulfide bonds.

These peptides are able to raise antibodies in immunization schedules using animal experimental models. Therefore, specific antibodies against them can be produced from these animals. These antibodies constitute another embodiment of this invention. They can be used in diagnosis to identify the native protein, either as part of a protein extract, or in the whole tuberculosis bacillus, and they may be included in a therapeutic schedule.

Naturally induced human antibodies, elicited against M. tuberculosis proteins, may also be able to react with any peptide fragment derived from Formula IV. Further contemplated is a diagnostic system for assaying the presence of antibody molecules to an antigen to a tuberculous mycobacterium in a body component such as body fluids or body tissues. Such a system comprises a solid support on a solid matrix to which the peptides are affixed.

Peptides corresponding to formulas V, VI, VII, VIII and IX have been shown to be able to stimulate lymphocyte proliferation of human peripheral blood cells in vitro. This indicates that these peptides may be used as tools to develop a skin test based on host cellular immune response, and probably a synthetic vaccine against M. tuberculosis.

DETAILED DESCRIPTION OF THE INVENTION

Applicant has established and determined the novel nucleotide sequence of an M. tuberculosis gene which encodes for the MPT protein, and is found to be present exclusively in M. tuberculosis bacilli. The nucleotide sequence of Formula I, its derived Formulas II and III, the 134 amino-acid protein of Formula IV, and its derived sequences, namely, Formulas V, VI, VII, VIII and IX, represent preferred embodiments of the present invention.

NUCLEOTIDE SEQUENCE

By screening a genomic expression library of M. tuberculosis, with a rabbit polyclonal serum raised against a M. tuberculosis protein, the gene for a species specific antigen was identified and termed MTP40. The coding portion of the gene consists of 402 base pairs ordered according to Formula I. Nucleotide sequences within the MTP40 gene were not found in genomic DNAs from related mycobacteria (*M. bovis, M. bovis BCG, M. fortuitum, M. phlei, M. vaccae, M. flavecens, M. smegmatis* and *M. leprae, S. epidermis, S. aureus, P. aeruginosa, P. vulgaris* or from Staphylococcus spp.) by either hybridization studies or by Polymerase Chain Reactions (PCR). Certain oligonucleotide segments from the gene, namely, Formulas II and III, have been used in PCR experiments to prove the absence of the gene in other mycobacterial species. The PCR technique has also been used with Formulas II and III, or their complementary formulas (the substitution of A for T, T for A, G for C, and C for G) to evaluate the presence of *M. tuberculosis* bacilli in different body components, e.g., tissues and fluids, indicated by the amplification of the MTP40 protein gene. Different oligonucleotides corresponding to random segments of the sequence over the entire gene have been assayed in hybridization studies with the same goal. These indicate that segments of the gene produced either by chemical synthesis, for example, by the phosphoramidite method, or by enzymatic methods, e.g., nick translation or random priming, can be used to specifically detect the original gene and, thus, since it is exclusively present in *M. tuberculosis* genome, the *M. tuberculosis* bacilli in samples where its presence is suspected. The use of such types of oligonucleotide probes, as well as the variations introduced therein, e.g., new restriction sites, linkers or base redundancies, in order to detect the MTP40 gene, or the whole *M. tuberculosis* bacillus for diagnostic purposes are contemplated as being embodied in this invention. The use of formulas I, II, or III, or their complementary sequences, as radioactive or non-radioactive probes for PCR or hybridization assays for diagnostic purposes is also contemplated as being embodied in this invention.

AMINO ACID SEQUENCE

The nucleotide sequence of Formula I encodes a polypeptide having 134 amino acids, that has been termed MTP40 protein (Formula IV). The molecular weight of the protein is estimated to be 13.8 kDa (kiloDaltons). Restriction segments of the protein gene have been cloned into phage and plasmid vectors in order to produce fragments of the MTP40 protein as fusion proteins. These recombinant proteins have been proven to react with antibodies elicited against the native protein, as well as with human antibodies produced by tuberculosis patients against the whole bacilli, thus indicating that the entire molecule or its segments can be expressed as foreign products in heterologous systems without disturbing their capacity to react with specific antibodies. It is contemplated that the use of the expressed products of the MTP40 gene, or any derived segment, to produce antibodies against the native protein or to detect the presence of such antibodies as part of any diagnostic method, is deemed to be embodied in the present invention.

SYNTHETIC PEPTIDES

A number of synthetic peptides, based on the amino acid sequence of the MTP40 protein, have been chemically synthesized according to the multiple solid phase system (MSPS), or by other standard methods. They have been used in a series of immunological studies as either antigens or as immunogens. These studies have led to the conclusion that the protein possesses various immunodominant B cell and T cell epitopes. Analyses by ELISA (Enzyme Linked Immunosorbent Assay) and Lymphocyte proliferation assay of synthetic peptides antigens from *M. tuberculosis* MTP40 protein have demonstrated that the MTP40 protein has immunodominant B cell and T cell epitopes, respectively, which correspond to different peptides that also represent a preferred embodiment of the present invention. Certain of these peptides, corresponding to Formulas V, VI, VII, VIII and IX were recognized to a significant extent by sera from tuberculosis patients, or were able to stimulate in vitro cellular proliferation of T lymphocytes obtained from tuberculosis patients. It is contemplated that when reference is made hereafter to these five(5) peptides, Formulas V, VI, VII, VIII and IX, it shall be understood to also include any other peptide derived from the MTP40 protein, i.e., any of its analogues.

The properties of the novel peptide compounds of the present invention make them suitable candidates for the early immunodiagnosis and detection of tuberculosis, as well as for determining the evolution of tuberculosis in patients. In the same manner, there are several of them which are promising synthetic antigens for a tuberculosis vaccine. When employed as antigens in ELISA testing, the testing is done in the following manner.

Overlapping peptides were synthesized from MTP40 protein using the multiple solid phase synthesis method, described by R. Houghten (Proc. Natl. Acad. Sci. U.S.A. 82:5131-5135, 1985). These peptides were used as antigens in ELISA testing, as well as in Lymphocyte proliferation assays.

Whole blood from twenty seven (27) individuals, clinically and bacteriologically diagnosed by positive sputum (B+) as being active pulmonary tuberculosis patients was obtained at the Santa Clara Lung Hospital in Bogota, Colombia. Also, seventeen(17) whole blood samples from active tuberculosis patients, who had B(+) sputum at the time of diagnosis, but whose sputum had become B(−), were obtained at the same hospital. Whole blood samples from twenty-five(25) healthy individuals were collected from among the families of the active tuberculosis patients. As normal controls, whole blood from nineteen(19) normal donors, which were without tuberculine test, was collected, among healthy student volunteers. Mononuclear cells were isolated from all samples in order to be used in lymphocyte proliferation assay and sera were maintained at 4° C. until its use in the ELISA test.

When employed coated in an ELISA microtiter plaque, at a level of 3 micrograms per well, the peptides corresponding to Formula V (S700), Formula VI (S702), Formula VII (S698) and Formula VIII (S708) provide significant data which make them viable candidates for the design of a method for the early detection by ELISA of infection by *Mycobacterium tuberculosis*, as well as for the prognosis of the disease. In the ELISA test, the recognition of the peptides by both active tuberculosis patients having B(+) and B(−) sputum and healthy individuals from tubercular households, demonstrate that the peptides are able to react with sera from individuals that have been in contact with the tuberculosis bacillus.

In general, the sera from active B(+) patients was recognized by each of peptides studied, namely, Formulas V, VI, VII and VIII. The most widely recognized was S700 (corresponding to the Formula V), which reacted with 54.8% of sera from these patients, while it was only recognized by 2.9% of sera from normal donors. Also, the other peptides S702, S698 and S708

(corresponding to the Formulas VI, VII and VIII, respectively) were tested with the same groups of individuals. The peptide called S702 was recognized by 28% of the B(+) patients; S698 was recognized by 20.8% of them and S708 reacted positively with 16% of the patients of the same group. On the other hand, the peptides' reaction with sera from normal donors was negligible. Some peptides were recognized by less than 5% of normal individuals, while other peptides were not recognized by anyone.

Sera of active tuberculosis patients having B(−) sputum exhibited the maximum reactivity with the antigen from the synthetic peptides of the present invention. The most widely recognized was the S702 peptide, which was recognized by 52.6% of these patients. The other three peptides showed a percentage recognition of not less than 36.8%, with sera of the same group.

From all serological date it can be concluded that the presence of MTP40 indicates infection by *M. tuberculosis*. Thus, the peptides can be used both as a reagent for monitoring the effects of chemotherapy (prognosis) and also for the early detection of infection by designing a suitable immunodiagnostic method.

With respect to Lymphocyte proliferation assay testing, 5 to 25 micrograms (μg) of the peptides of Formulas V, VI, VII, VIII and IX were employed. This T-cell recognition test provided important data which raises the distinct possibility of their candidacy for eventual use in a tuberculosis vaccine.

Overlapping peptides were synthesized from MTP40 protein in order to be tested with T-cells from groups of different individuals. In the Lymphocyte proliferation test, all the peptides were recognized by the groups studied, thus indicating that the synthetic peptides are able to induce reactivity in active tuberculosis patients and also in those individuals who have experienced long-term exposure to the mycobacterium bacillus. However, each group studied reacted in a different manner with these peptides. Healthy households were the strongest responders to all the peptides. The most widely recognized was the S708 (corresponding to Formula VIII), which reacted with 60% of the T-cells from healthy individuals from tubercular households, while it was only recognized by 11% of active tuberculosis patients having B(+) sputum and 0% of normal donors. The other three peptides S700, S702 and S704 (corresponding to the Formulas V, VI and IX, respectively) were also tested with the same groups: S700 was recognized by 44% of healthy individuals from households where tuberculosis was present, 3.4% of active tuberculosis patients and 0% of normal donors; the S702 was recognized by 44% of healthy individuals from tubercular households, 3.4% of active patients and 0% of normal donors; the S704 peptide was recognized by 40% of individuals from tubercular households, by 0% of active patients having B(+) sputum and by 0% of normal donors.

These data show that there is a significant correlation between an increased recognition of these peptides and the healthy individuals in tuberculosis-containing households, thus indicating that these peptides, and specifically the S708 peptide (Formula VIII), could well play a fundamental and significant role in the acquired cellular resistance to mycobacterium infection, which would make this peptide a suitable candidate to be a subunit in an eventual synthetic vaccine against tuberculosis.

As employed herein, the following abbreviations shall be deemed to have the following meanings:

| | |
|---|---|
| Boc-tertiary = | butoxycarbonyl |
| But-tertiary = | butyl (as ether forming group) |
| DCC = | dicyclohexylcarbodiimide |
| DIPCD = | diisopropylcarbodiimide |
| DCM = | dichloromethane |
| DMF = | dimethylformamide |
| DIEA = | diisopropylethylamide |
| TFA = | trifluoroacetic acid |
| HF = | hydrogen fluoride |
| Ala = | alanine |
| Arg = | arginine |
| Asn = | asparagine |
| Cys = | cysteine |
| Gly = | glycine |
| Glu = | glutamic acid |
| Phe = | phenylalanine |
| Leu = | leucine |
| Val = | valine |
| Tyr = | tyrosine |
| Thr = | threonine |
| Met = | methionine |
| His = | histidine |
| Lys = | lysine |
| Pro = | proline |
| Ser = | serine |
| Ile = | isoleucine |
| Asp = | aspartic acid |
| Gln = | glutamine |
| Trp = | tryptophan |

EXAMPLE 1

General Procedure for the Amplification of MTP40 Gene by the Polymerase Chain Reaction (PCR) Technique.

The *M. tuberculosis* DNA is purified from the bacilli by enzymatic digestion with lysozyme (Sigma Chem. Co.) and Proteinase K (Sigma Chem. Co.). Thereafter, an extraction with phenol-chloroform is carried out and the DNA is obtained by alcohol precipitation. The PCR is done by adding 20 mM of primers PT1 (Formula II) and PT2 (Formula III) to the purified *M. tuberculosis* DNA in different concentrations (1 μg—10 fg). Denaturing is carried out at a temperature of 94° C. for one minute; the annealing and extension reactions are carried out at 74° C. for 2 minutes; and the cycle is repeated thirty(30) times. Buffers, deoxynucleotide triphosphates (dNTP) and Polymerase enzyme (TAQ polymerase) are obtained by Cetus Corporation and used pursuant to their instructions.

The amplified product is visualized by agarose gel electrophoresis stained with Ethidium Bromide (Sigma Chem. Co.,) and subsequently hybridized with a radioactive probe derived from the nucleotide sequence of MTP40 gene.

EXAMPLE 2

General Procedure for the Solid Phase Synthesis of the Peptide Compounds of the Present Invention.

Solid phase peptide synthesis (SPPS) is employed according to the method originally described in 1963 by M. B. Merrifield, as modified by R. A. Houghten, using propylene bags simultaneously. The method involves the coupling of amino acids from the carboxy-terminal end to the N-terminal end of the peptide, once the amino acid is attached to an insoluble solid support.

The polystyrene resin solid support employed is a copolymer of styrene with about 1% to 2% by weight of divinyl benzene as a cross-linking agent, which causes the polystyrene polymer to be completely insoluble in most organic solvents and which causes it to swell extensively in DCM and DMF. This allows the penetration and free transit of solvents and reagents, thus permitting the various chemical reactions to proceed.

The solid support is made functional by the introduction of the insoluble P-methylbenzhydramine. HCL (P-MBHA) resin having free amino groups (0.4 to 0.6 miliequivalents per gram of resin). The resin is swollen by three washes of ten minutes each with DCM with constant stirring. The acidic groups are neutralized with 5% DIEA in DCM to permit attachment of the first amino acid.

The attachment is accomplished by dissolving a tenfold excess of Boc-amino acid in 10 milliliters of DCM, or in a mixture of DCM: DMF (2:1), and activated with ten equivalents of DIPCD in four milliliters of DCM. This mixture is employed to couple the first amino acid via its carboxyl groups to the activated resin. To assure complete coupling, it is checked by the picrate reaction.

After the first amino acid has been attached, an amino acyl resin has been formed which is used to add the other Boc-amino acids in the desired sequence via a series of steps which results in elongation of the peptide chain.

The steps are as follows:

1. Acid deprotection of the N-terminal group of the attached Boc-acid. Selective removal of the Boc-group is accomplished with 55% TFA in DCM for 30 minutes.

2. Neutralization of excess acid with 5% DIEA in DCM.

3. Activation and coupling of next Boc-amino acid. A Boc-amino acid which was previously activated with DIPCD is coupled to the amino acyl resin to form the peptide bond. The excess of coupled amino acid is then removed by filtration and the amount of coupled Boc-amino acid is determined by the picrate reaction. Then the cycle is commenced once again.

EXAMPLE 3

Lymphocyte Proliferation Assay

The following method was employed in conducting the Lymphocyte Proliferation Assay.

Peripheral blood mononuclear cells (PBMC) were isolated from heparinized whole blood by Ficoll-Hypaque 1077 (SIGMA poole, England), centrifuged and suspended in growth medium (RPMI 1640: Flow Labs) containing 10% of calf fetal serum (CFS), 2 mM L-glutamine, 25 mM Hepes, 100 IU penicillin per ml., and 40 micrograms ($\mu$g) of streptomycine per ml. Then $1.5 \times 10^5$ cells per well were cultured with antigen in a 96-well-flat-bottomed microtiter plates (NUNC. Denmark) for 5 to 6 days at 37° C. in humidified air with 5% $CO_2$. The cells were then pulsed (0.8 uci-well) with (methyl-3H) thymidine (Amercham Inter. U.K.) After approximately 16 hours, they were harvested onto glass fiber filter strips and the quantity of (3H) thymidine incorporated was measured by a liquid scintillation counter in a Beckmann L-9000. All antigen-containing cultures were performed in triplicate and converted to stimulation indices (SI) in relation to the medium control culture. Values are expressed as mean cpm +/− standard deviation (SD).

Lymphocyte proliferation to the antigen was considered positive when the stimulation indices values were more than 3SD above mean values obtained in the 22 normal donors.

The functional viability of the lymphocytes, following isolation on a Fycoll-Hypaque density gradient, was evaluated by Con-A responsiveness. Background proliferation in cpm were between 300 to 5500 and all lymphocyte samples were tested with two antigen doses, namely, 5 and 25 $\mu$g/ml. The results at each concentration demonstrated that the peptides need an adequate dose to be recognized.

EXAMPLE 4

The ELISA testing was performed in accordance with the following method.

Four 96 microwell plates were coated with each of the four peptides, namely, Formulas V, VI, VII and VIII, prepared in accordance with Example 2. 150 $\mu$l per well of a solution of 10 $\mu$g/ml of each peptide in coating buffer ($NaHCO_3$—$Na_2CO_3$ 0.1M, pH 9.2) was left 1 hour at 37° C., then for 48 hours at 40° C. and, finally, 1 hour at 37° C. in high binding capacity microwell modules (NUNC ref: 4-69914). Also, for each plate, control wells were coated in the same manner.

After washing the plates 2 times with PBS plus 0.05% Tween 20 (PBST), 100 $\mu$l per well of each serum were added in 1:20 dilution in PBST with 1% goat serum as a blocking agent (PBST-GS). The sera were incubated for 1 hour at 37° C. Then the plates were washed 5 times with PBST, and after adding 100 $\mu$l per well of anti-human IgG (Immunoglobulin G) peroxidase conjugate (SIGMA A-8785), diluted 1:1000 (v/v) in PBST-GS, were incubated for 1 hour at 37° C. The plates were then washed 5 times with PBST, and 100 $\mu$l of substrate solution (25 mg of O-phenylenediamine and 30 $\mu$l of $H_2O_2$ per 10 ml of citrate phosphate buffer at pH 5.0) were added.

The reaction was performed at room temperature in darkness for 5 minutes and was then stopped by adding 50 $\mu$l per well of 2N sulfuric acid.

Equal number of sera from each group of individuals were placed on the plate. 100 $\mu$l per well of sera from each group of individuals in the appropriate dilution, were placed in duplicate on the plate were added on every peptide coated well. The following steps were made according to the method described above.

By employing the method described above, it has been determined that the peptide compounds corresponding to the Formulas:

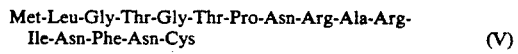
Met-Leu-Gly-Thr-Gly-Thr-Pro-Asn-Arg-Ala-Arg-Ile-Asn-Phe-Asn-Cys     (V)

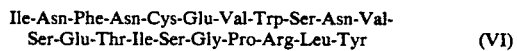
Ile-Asn-Phe-Asn-Cys-Glu-Val-Trp-Ser-Asn-Val-Ser-Glu-Thr-Ile-Ser-Gly-Pro-Arg-Leu-Tyr     (VI)

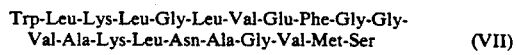
Trp-Leu-Lys-Leu-Gly-Leu-Val-Glu-Phe-Gly-Gly-Val-Ala-Lys-Leu-Asn-Ala-Gly-Val-Met-Ser     (VII)

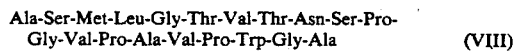
Ala-Ser-Met-Leu-Gly-Thr-Val-Thr-Asn-Ser-Pro-Gly-Val-Pro-Ala-Val-Pro-Trp-Gly-Ala     (VIII)

when tested by ELISA, can be used successfully as a means of monitoring the reagents of chemotherapy (prognosis) and for the early detection of infection (as suitable candidates for the design of a diagnostic method).

The terms and expressions which have been employed are used as terms of description and not of limitation, and there is no intention in the use of such terms and expressions of excluding any equivalents or features shown and described or any portions thereof, but it is recognized that various modifications are possible within the scope of the invention as claimed.

What is claimed is:

1. A diagnostic or taxonomic typification system for assaying for the presence of *M. tuberculosis* comprising:

(a) an oligonucleotide of the formula

ATGCTCGGCAACGCGCCGTCGGTGGTTCCCAACACCA

CGTTAGGGATGCACTGCGGCAGC

TTCGGCAGCGCTCCCAGCAACGGGTGGCTCAAGTTGG

GTCTGGTCGAATTCGGTGGAGTC

GCAAAGTTGAACGCTGAGGTCATGTCGCCAACCACGC

CGTCGCGCCAGGCGGTCATGTTG

GGAACCGGCACGCCGAACCGGGCGCGAATCAACTTCA

ATTGCGAGGTGTGGTCGAACGTG

TCGGAGACCATCAGCGGGCCGCGGCTGTACGGCGAAA

TGACAATGCAGGGAACGCGAAAA

CCCAGACCGAGCGGACCACGAATGCCACCGGACCCGG

GTACTGCGTCGATGTTGGGCACC

GTGACGAATTCGCCGGGTGTCCCGGCGGTGCCGTGGG

GGGCGTGA wherein the nucleotides are written from left-to-right according to their 5' to 3' order or any derived fragment therefrom greater than 15 nucleotides in length; and (b) indicating means for signalling the reaction of the oligonucleotide of (a) or any derived fragment therefrom greater than 15 nucleotides in length with a nucleic acid molecule.

2. The diagnostic system of claim 1 which employs the nucleotide sequence complementary to the formula

ATGCTCGGCAACGCGCCGTCGGTGGTTCCCAACACCA

CGTTAGGGATGCACTGCGGCAGC

TTCGGCAGCGCTCCCAGCAACGGGTGGCTCAAGTTGG

GTCTGGTCGAATTCGGTGGAGTC

GCAAAGTTGAACGCTGAGGTCATGTCGCCAACCACGC

CGTCGCGCCAGGCGGTCATGTTG

GGAACCGGCACGCCGAACCGGGCGCGAATCAACTTCA

ATTGCGAGGTGTGGTCGAACGTG

TCGGAGACCATCAGCGGGCCGCGGCTGTACGGCGAAA

TGACAATGCAGGGAACGCGAAAA

CCCAGACCGAGCGGACCACGAATGCCACCGGACCCGG

GTACTGCGTCGATGTTGGGCACC

GTGACGAATTCGCCGGGTGTCCCGGCGGTGCCGTGGG

GGGCGTGA wherein T is substituted for A, A is substituted for T, G is substituted for C, and C is substituted for G or any derived fragment greater than 15 nucleotides in length.

3. The diagnostic system of claim 1 which employs a compound of the formula PT1 5 CAACGCGCCGTCGGTGG 3 or any derived fragment greater than 15 nucleotides in length.

4. The diagnostic system of claim 1 which employs a compound of the formula PT2 5 CCCCCCACGGCACCGC 3 or any derived fragment greater than 15 nucleotides in length.

5. A diagnostic system for assaying for the presence of *M. tuberculosis* in a sample of body fluids or body tissues containing antibodies or cells comprising:

(a) an isolated protein of the formula

Met—Lys—Gly—Asn—
   Ala—Pro—Ser—Val—Val—Pro—Asn—Thr—Thr—Leu—Gly—
   Met—His—Cys—Gly—Ser—
   Phe—Gly—Ser—Ala—Pro—Ser—Asn—Gly—Trp—Leu—Lys—
   Leu—Gly—Leu—Val—Glu—
   Phe—Gly—Gly—Val—Ala—Lys—Leu—Asn—Ala—Glu—Val—
   Met—Ser—Pro—Thr—Thr—
   Pro—Ser—Arg—Gln—Ala—Val—Met—Leu—Gly—Thr—Gly—
   Thr—Pro—Asn—Arg—Ala—
   Arg—Ile—Asn—Phe—Asn—Cys—Glu—Val—Trp—Ser—Asn—
   Val—Ser—Glu—Thr—Ile—
   Ser—Gly—Pro—Arg—Leu—Tyr—Gly—Glu—Met—Thr—Met—
   Gln—Gly—Thr—Arg—Lys—
   Pro—Arg—Pro—Ser—Gly—Pro—Arg—Met—Pro—Pro—Asp—
   Pro—Gly—Thr—Ala—Ser—
   Met—Leu—Gly—Thr—Val—Thr—Asn—Ser—Pro—Gly—Val—
   Pro—Ala—Val—Pro—Trp—
   Gly—Ala written from left-to-right in the direction of the amino-terminus to the carboxy-terminus; and (b) indicating means for signalling the immunoreaction of the isolated protein (a) with a sample of body fluids or body tissues containing antibodies or cells.

6. The diagnostic system of claim 5 which employs a compound of the formula Met-Leu-Gly-Thr-Gly-Thr-Pro-Asn-Arg-Ala-Arg-Ile-Asn-Phe-Asn-Cys.

7. The diagnostic system of claim 5 which employs a compound of the formula Ile-Asn-Phe-Asn-Cys-Glu-Val-Trp-Ser-Asn-Val-Ser-Glu-Thr-Ile-Ser-Gly-Pro-Arg-Leu-Tyr.

8. The diagnostic system of claim 5 which employs a compound of the formula Trp-Leu-Lys-Leu-Gly-Leu-Val-Glu-Phe-Gly-Gly-Val-Ala-Lys-Leu-Asn-Ala-Glu-Val-Met-Ser.

9. The diagnostic system of claim 5 which employs a compound of the formula Ala-Ser-Met-Leu-Gly-Thr-Val-Thr-Asn-Ser-Pro-Gly-Val-Pro-Ala-Val-Pro-Trp-Gly-Ala.

10. The diagnostic system of claim 5 which employs a compound of the formula Gly-Pro-Arg-Leu-Tyr-Gly-Glu-Met-Thr-Met-Gln-Gly-Thr-Arg-Lys-Pro-Arg-Pro-Ser-Gly-Pro.

* * * * *